United States Patent [19]

Enemark

[11] 4,430,646
[45] Feb. 7, 1984

[54] FORWARD SCATTER SMOKE DETECTOR

[75] Inventor: Robert B. Enemark, Duxbury, Mass.

[73] Assignee: American District Telegraph Company, Jersey City, N.J.

[21] Appl. No.: 221,524

[22] Filed: Dec. 31, 1980

[51] Int. Cl.³ .............................................. G08B 17/10
[52] U.S. Cl. .................................... 340/630; 250/574; 356/439
[58] Field of Search ............... 340/630, 380; 250/574; 356/338, 339, 247, 438, 439

[56] References Cited

U.S. PATENT DOCUMENTS

| | | | |
|---|---|---|---|
| 3,185,975 | 5/1965 | Kompelien | 250/574 X |
| 3,409,885 | 11/1968 | Hall | 340/630 |
| 3,710,365 | 1/1973 | Barnes | 340/630 X |
| 3,787,703 | 1/1974 | Topol | 250/574 |
| 4,111,564 | 9/1978 | Trice, Jr. | 356/247 |
| 4,181,439 | 1/1980 | Tresch et al. | 250/574 X |
| 4,230,950 | 10/1980 | Forss et al. | 340/630 X |
| 4,241,282 | 12/1980 | Tresch et al. | 250/574 |
| 4,269,510 | 5/1981 | Horvath et al. | 356/338 |

Primary Examiner—John W. Caldwell, Sr.
Assistant Examiner—Daniel Myer
Attorney, Agent, or Firm—James H. Grover

[57] ABSTRACT

An optical smoke detector having a conical masking body located directly between a light source and a light receiver. The masking body is provided with a reflecting surface so that rays from the light source are diverted into a reaction zone to supplement direct rays from the light source to the zone. In one embodiment the reflecting surface is cuspidate while in another embodiment a second masking body is added which shadows the light receiver from viewing the base of the first masking body.

5 Claims, 3 Drawing Figures

4,430,646

FORWARD SCATTER SMOKE DETECTOR

BACKGROUND OF THE INVENTION

With the type of optical smoke detector in which smoke scatters light from an exciter lamp to a photocell there is a choice of disposing lamp and cell so that light is scattered backward or forward from the smoke as in Kompelien, U.S. Pat. No. 3,185,975. Forward scatter disposition has the advantage that particles scatter more incident light forward than backward, but on the other hand requires that light from the lamp must be masked from direct paths to the photocell, as in Hall, U.S. Pat. No. 3,409,885. The masking means hitherto has absorbed a substantial amount of the source light (as is recognized in Tresch, U.S. Pat. No. 4,181,439). This involves an energy loss of considerable importance in battery powered smoke detectors widely used in residences.

It is therefore an object of the present invention to provide a forward scatter type of smoke or other particle detector which conserves light energy.

SUMMARY OF THE INVENTION

According to the invention a particle detector comprises a source of light directed on a first path accessible to particles; a photocell having a photosensitive area viewing on a second path into a zone of intersection of the two paths and responsive to light scattered from particles in the zone; and a body masking direct light from the source to the photosensitive area and having a periphery outside which light passes to the intersection zone; wherein the detector includes a reflective surface disposed between the masking body periphery and the light source having reflective components at an angle relative to direct rays from the source toward the masking body such as to direct such rays away from the body into the intersection zone.

The term photocell is meant to include all photoelectric cells including those of the tube, resistance, voltaic and diode types.

Preferably the reflective surface is cone like, by which is meant conical and cuspidate surfaces, usually surfaces of revolution. The reflective surface may, however, be planar, that is a flat or warped plane.

DRAWING

DESCRIPTION

Figure 1:
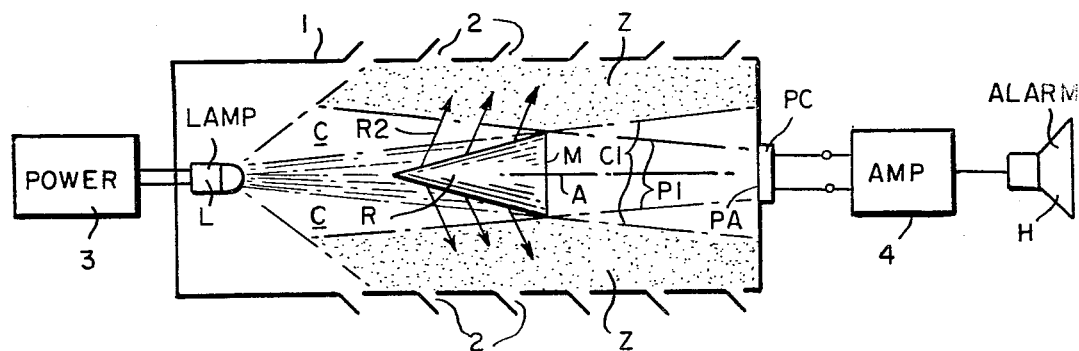
FIG. 1 is a schematic sectional view of one form of smoke detector.

As shown in FIG. 1 a forward scatter, optical smoke detector comprises a housing 1 which encloses a dark reaction chamber to which smoke has access through louvres 2 or a modern baffle system, such as is shown in Marsocci et al, U.S. Pat. No. 4,206,366. At one end of the dark chamber is a lamp L which may have spaced or integral lenses associated with it, and which is lighted by a steady or pulsed power source 3. At the other end of the chamber is a photocell PC having a photosensitive area PA. The cell is connected to amplifying, threshold and alarm circuits 4, such as are shown in Cooper, U.S. Pat. No. 4,193,069, driving an alarm horn H. On an axis A through the lamp L and cell PA is located a conical masking body M which shields the photosensitive area PA from the direct rays from the lamp L.

The lamp, mask and cell define three optical patterns. From the lamp light is directed by the lamp lens on a hollow conical path C whose scope is from about 90° to either side of the lamp to innermost rays C1 which pass the periphery of the masking body M. The photocell PC views the dark chamber on a second hollow conical path bounded by the housing 1 on the outside and the innermost lines P1 masking body M on its inside. The two paths overlap in the dotted intersection or reaction zone Z which is the reaction volume in which smoke particles scatter light from the source lamp L to the photocell PC. If the masking body presented a flat, light absorbing surface to the lamp L up to fifty percent of the light would be wasted.

According to the present invention the light normally wasted by absorption in the mask M is retrieved by providing a reflecting surface R between the forward surface of the masking body M and the lamp L. In FIG. 1 the surface is a simple conical surface of revolution about the axis A. This reflective surface is disposed at such an angle that rays from the lamp toward the masking body which were previously wasted by absorption or reflection out of the view of the cell are diverted into the intersection or reaction zone Z where they supplement the direct rays from the lamp to the zone and increase the sensitivity of the detector to smoke.

Figure 2:
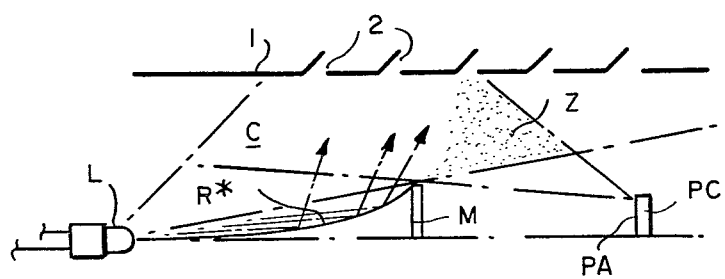
FIGS. 2 and 3 are similar schematic views of other forms of detector.

FIG. 2 illustrates forms of the invention in which the reflecting surface R* is not conical but still cone like or cuspidate. A cuspidate warped planar surface or a cuspidate surface of revolution of a curved line reflects light more efficiently into the intersection zone.

Figure 3:
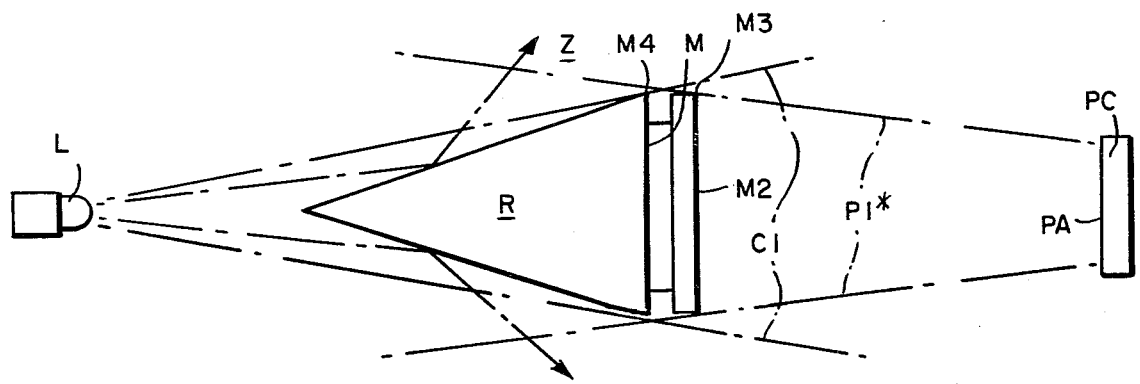

The periphery M4 of the masking disc M nearest the photocell can act as an undesirable light scatterer, particularly if dust builds up on the edge or if the disc is very thin. The base of the reflecting cone of FIG. 1 presents essentially the same problem as a thin disc in scattering light around its edge, even more so if dust builds up there. This is undesirable, since if this light is bent directly to the photocell it can create a false signal that might cause a false alarm or at least reduce the ratio of signals between the alarm and clear air condition (reduced signal to unwanted noise signal ratio). FIG. 3 shows the addition of a second masking body M2 which shadows the photocell from viewing the base of the first masking body M so that light scattered at the latter's edge M4 is inside the innermost lines P1* of the view of the cell and will not be detected. It is also necessary to place the second disc in the shadow of the first disc inside the innermost lamp rays C1 with its periphery M3 shielding the periphery M4 of the first body M so that the light from the lamp cannot illuminate its edge. It is further desirable to minimize the reduction in angle-of-view of the photocell by the second masking body, so as not to appreciably reduce system efficiency.

It should be understood that the present disclosure is for the purpose of illustration only and that this invention includes all modifications and equivalents which fall within the scope of the appended claims.

What is claimed is:

1. A particle detector comprising:
   a source of light directed on a first path accessible to particles;
   a photocell having a photosensitive area viewing on a second path into a zone of intersection of the two paths and responsive to light scattered from particles in the zone; and a body masking direct light from the source to the photosensitive area and having a periphery outside which light passes to the intersection zone;

wherein the detector includes a reflective surface disposed between the masking body periphery and the light source having reflective components at an angle relative to direct rays from the source toward the masking body such as to direct such rays away from the body into a substantial value of the intersection zone; and wherein the reflective surface is cone like.

2. A detector according to claim 1 wherein the reflective surface is a surface of axial revolution.

3. A detector according to claim 2 wherein the reflective surface is a surface of revolution of a curved line.

4. A detector according to claim 2 wherein the light source and photocell are on the axis of revolution.

5. A detector according to claim 1 wherein the surface has a conical apex directed toward the light source and the surface flares away from the light source.

* * * * *